US008322303B2

(12) United States Patent
Chang

(10) Patent No.: US 8,322,303 B2
(45) Date of Patent: *Dec. 4, 2012

(54) METHOD FOR TREATING SWINE FECES/URINE

(75) Inventor: Chun-Hsung Chang, Chang-Hua Hsien (TW)

(73) Assignee: New I Ten Rin Enterprise Co., Ltd., Chang-Hua Hsien (TW)

( * ) Notice: Subject to any disclaimer, the term of this patent is extended or adjusted under 35 U.S.C. 154(b) by 184 days.

This patent is subject to a terminal disclaimer.

(21) Appl. No.: 12/955,998

(22) Filed: Nov. 30, 2010

(65) Prior Publication Data

US 2012/0132141 A1 May 31, 2012

(51) Int. Cl.
*A01K 29/00* (2006.01)

(52) U.S. Cl. .......................... 119/6.5; 119/6.6

(58) Field of Classification Search .................. 119/6.5, 119/6.6; 424/76.5, 76.6
See application file for complete search history.

(56) References Cited

U.S. PATENT DOCUMENTS

| | | | |
|---|---|---|---|
| 4,594,964 A * | 6/1986 | Vargas et al. | 119/6.6 |
| 6,557,487 B1 * | 5/2003 | Fleischmann | 119/6.5 |
| 6,938,574 B2 * | 9/2005 | Zhang | 119/6.6 |
| 2002/0177219 A1 * | 11/2002 | Olivier | 435/262 |
| 2003/0143728 A1 * | 7/2003 | Olivier | 435/290.1 |
| 2003/0233982 A1 * | 12/2003 | Zhang | 119/6.5 |
| 2004/0089241 A1 * | 5/2004 | Zhang | 119/6.5 |
| 2011/0296756 A1 * | 12/2011 | Zhang | 47/59 R |

OTHER PUBLICATIONS

Larry Newton Using the Black Soldier Fly, *Hermetia illucens*, Value added tool for the Management of swine manure, North Carolina State University (USA) Jun. 2006.*

Joseph Diclaro and Phillip Kaufman 'Black soldier fly *Hermetia illucens* Linnaeus (insecta: Diptera: Stratiomyidae)' EENY-461, IFAS Extension, University of Florida (USA), Jun. 2009.*

* cited by examiner

*Primary Examiner* — Isam Alsomiri
*Assistant Examiner* — Justin Benedik
(74) *Attorney, Agent, or Firm* — Alan Kamrath; Kamrath IP Lawfirm, PA

(57) ABSTRACT

A method for treating swine feces/urine includes breeding and growing imagoes of *Musca Domestica* in an environment having a temperature of 18-35° C. and having a humidity of 50-80%. The imagoes of *Musca Domestica* lay eggs in the environment. The eggs of *Musca Domestic* are transferred into a cultivating material including at least one product of soybean and/or milk. The eggs of *Musca Domestica* are bred at a temperature of 20-35° C. until hatching into larvae. The larvae of *Musca Domestica* are placed on swine feces/urine of a thickness of 4-10 cm at a temperature of 20-35° C. for 2-3 days. The larvae feed on and decompose the swine feces/urine. The swine feces/urine can be decomposed in 5-7 days without causing pollution to the air, water sources, and environment.

13 Claims, 1 Drawing Sheet

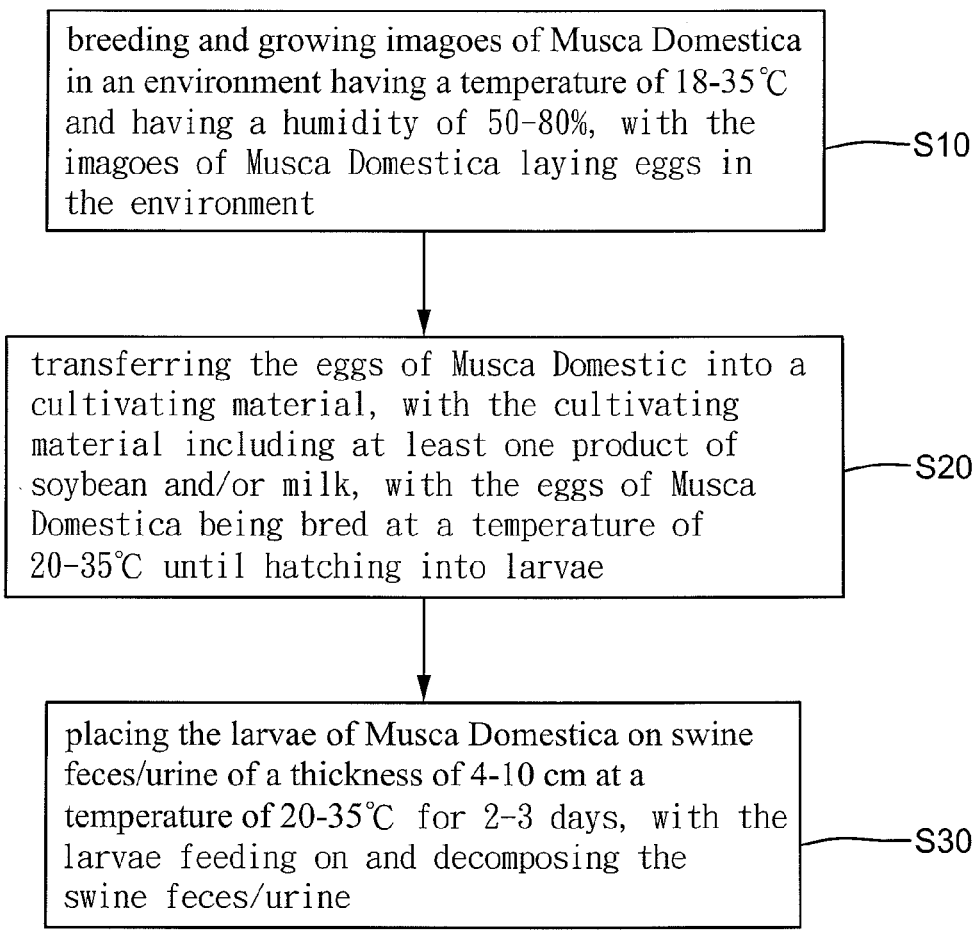

METHOD FOR TREATING SWINE FECES/URINE

BACKGROUND OF THE INVENTION

The present invention relates to a method for treating feces of livestock and, more particularly, to a method for treating swine feces/urine.

Cultivation of swine is an important role of the livestock industry in our country. A huge amount of swine feces/urine is produced along with the increase in the number and scale of the cultivating sites, leading to pollution to the air, rivers, and lakes as well as other environmental problems. Traditionally, the swine feces/urine are mixed with dry leaves and straws to form compost that is then composted on farm lands. However, the composting procedure takes about four to five months, which is time-consuming and inefficient. Furthermore, ozone is generated during the composing period, causing smell and air pollution. Further, mosquitoes and flies are attracted by and propagate on the compost. The mosquitoes and flies are media of diseases, causing a dirty environment and increasing the possibility of disease infection to the human bodies. Nowadays, farmers rely on chemical fertilizers instead of compost such that treatment of swine feces/urine becomes tricky.

Although the government intends to build wastewater treating facility to treat feces, the wastewater treating facility is expensive and has low revenue from the substances obtained after treatment. Furthermore, the wastewater treating facility is not available in every cultivating area. Further, some of the swine cultivators are not familiar with operation of the wastewater treating facility, leaving to accumulation of sludge at the effluent ports. Other swine cultivators directly discharge the swine feces/urine into the environmental water sources, greatly polluting the water and air and causing problems to nearby habitants. Up to 1,700,000 swine are cultivated in Pintong County having the most swine cultivators in Taiwan. Pollution of the water sources and air will occur if the huge amount of swine feces/urine and sludge discharged every day is not properly treated.

Thus, a need exists for a method for efficiently treating swine feces/urine.

BRIEF SUMMARY OF THE INVENTION

To solve the disadvantages and problems in traditional composting method and other swine feces/urine treating methods, the present invention provides a method for treating swine feces/urine including breeding and growing imagoes of *Musca Domestica* in an environment having a temperature of 18-35° C. and having a humidity of 50-80%. The imagoes of *Musca Domestica* lay eggs in the environment. The eggs of *Musca Domestic* are transferred into a cultivating material including at least one product of soybean and/or milk. The eggs of *Musca Domestica* are bred at a temperature of 20-35° C. until hatching into larvae. The larvae of *Musca Domestica* are placed on swine feces/urine of a thickness of 4-10 cm at a temperature of 20-35° C. for 2-3 days. The larvae feed on and decompose the swine feces/urine.

Preferably, the temperature of the environment in which the imagoes of *Musca Domestica* grow and lay eggs is 24-26° C.

Preferably, the humidity of the environment in which the imagoes of *Musca Domestica* grow and lay eggs is 54-56%.

The cultivating material preferably has a water content of 80-95% by weight and more preferably 92% by weight.

Preferably, the cultivating material is received in a Petri dish.

Preferably, 2-4 grams of the eggs of *Musca Domestica* are transferred per kilogram of the cultivating material.

Preferably, the imagoes of *Musca Domestica* lay eggs after the imagoes of *Musca Domestica* have grown 1-3 days.

Preferably, the eggs of *Musca Domestica* hatch into the larvae in 1-2 days.

Preferably, the swine feces/urine are received in a Petri dish.

The swine feces/urine preferably have a water content of 80-95% by weight and more preferably 92% by weight.

The method for treating swine feces/urine according to the present invention uses the larvae of *Musca Domestica* to decompose and, thus, treats the swine feces/urine.

The swine feces/urine can be treated in 5-7 days. Compared to other methods for treating swine feces/urine that causes pollution, the method according to the present invention will not cause adverse affect and pollution to the air, water sources, and environmental sanitary. Furthermore, the tools and equipment required in the method according to the present invention are simple and easy to operate, which is suitable for swine cultivating sites. After treatment of swine feces/urine, beneficial organic fertilizer can be obtained from the excretion of the larvae of *Musca Domestica*. Furthermore, the excretion of the larvae of *Musca Domestica* can be processed into a nutrient additive to increase the benefits of the swine cultivators while preventing pollution and increasing the yield of swine.

The present invention will become clearer in light of the following detailed description of illustrative embodiments of this invention described in connection with the drawing.

DESCRIPTION OF THE DRAWING

The drawing shows a block diagram illustrating a method for treating swine feces/urine according to the present invention.

DETAILED DESCRIPTION OF THE INVENTION

With reference to the drawing, to efficiently treat swine feces/urine and to avoid pollution to the air and water, the present invention provides a method for treating swine feces/urine including breeding and growing imagoes of *Musca Domestica* (house flies) in an environment having a temperature of 18-35° C. and having a humidity of 50-80%. The imagoes of *Musca Domestica* lay eggs in the environment (S10). The eggs of *Musca Domestic* are transferred into a cultivating material including at least one product of soybean and/or milk. The eggs of *Musca Domestica* are bred at a temperature of 20-35° C. until hatching into larvae (S20). The larvae of *Musca Domestica* are placed on swine feces/urine of a thickness of 4-10 cm at a temperature of 20-35° C. for 2-3 days. The larvae feed on and decompose the swine feces/urine (S30). Examples of the method for treating swine feces/urine according to the present invention will now be described.

EXAMPLE 1

Breeding of Imagoes of *Musca Domestica*

An appropriate number of wild *Musca Domestica* were placed in a space and fed with the same food. The wild *Musca Domestica* was tamed after several generations of breeding and propagation, obtaining suitable *Musca Domestica*. The pupae of the tamed *Musca Domestica* before eclosion were placed in an eclosion plate placed in a breeding cage for imagoes. The breeding cage was a sealed net cage having a size of 100-120 cm×60-80 cm×100-200 cm. The imagoes could not fly out of the breeding cage. Furthermore, the breeding cage was placed in a breeding room. The temperature of the breeding room was preferably of 18-35° C., most preferably 24-26° C. The humidity of the breeding room was preferably 50-80%, more preferably 54-56%. Further, the number of imagoes of *Musca Domestica* in the breeding cage was preferably 40,000-120,000. The breeding cage was under the light for 8-16 hours. Since the imagoes do not lay eggs in a dark environment, the breeder can adjust the period of time of the light and the dark according to the time the eggs are to be fetched. Furthermore, a tag can be affixed to the breeding cage to indicate the date on which the imagoes laid eggs and the number of eggs for control purposes.

The pupae of *Musca Domestica* turned into imagoes in 3 or 4 days. After eclosion, a food plate and a water plate were placed into the breeding cage for the imagoes. The foodstuff in the food plate included dairy products (such as milk powders) and sugar that imagoes are fond of. The imagoes began to lay eggs in 1-3 days after eclosion. A laying pan was placed into the breeding cage at that time. A laying pad was received in the laying pan. Substances such as fermented food (fermented milk or the like) capable of attracting the imagoes of *Musca Domestica* were adhered to the laying pad to attract the imagoes to lay eggs on the laying pad. The eggs were gathered periodically, and the laying pad was replaced.

EXAMPLE 2

Breeding of Larvae of *Musca Domestica*

An appropriate number of eggs of *Musca Domestica* were transferred into a plurality of first Petri dishes. 70-80% of the volume of each first Petri dish was filled with a cultivating material (about 6-8 cm in thickness). The cultivating material included at least one product of soybean and/or milk. A water content of the cultivating material was 80-95% by weight and more preferably 92% by weight. Namely, the solid content of the product of soybean and/or milk of the cultivating material was 5-20% by weight and more preferably 8% by weight. The eggs of *Musca Domestica* were bred at a temperature of 20-35° C. for several days until hatching into larvae (i.e., maggots). The water containing cultivating material provided a moist, nutritive environment for the larvae after hatching. This was the first-stage breeding.

The number of eggs was decided according to the amount of cultivating material received in each first Petri dish. Namely, it was estimated how many larvae could feed on the amount of cultivating material to estimate the number of eggs to be transferred into each first Petri dish. In an example, 2-4 grams of eggs of *Musca Domestica* were transferred per kilogram of cultivating material. The breeding underwent 1-2 days. Each first Petri dish was, but not limited to, a small container having a diameter of 10-12 cm and a height of 8-10 cm.

EXAMPLE 3

Treatment of Swine Feces/Urine

Swine feces/urine were placed into a plurality of second Petri dishes to a thickness of 4-10 cm. The swine feces/urine had a water content of 80-95% by weight and more preferably 92% by weight. An appropriate number of larvae obtained in the first-stage breeding was placed on the swine feces/urine and bred at a temperature of 20-35° C. for 2-3 days. During the breeding period, the larvae fed on the swine feces that provided a moist, nutritive environment for the larvae. This was the second-stage breeding during which the larvae grew and nourished by the nutritive ingredients in the swine feces/urine. The swine feces/urine eaten by the larvae were decomposed by the special enzymes in the larvae and then excreted out of the larvae. The excretion of the larvae can be used as excellent organic fertilizer. The whole process of decomposing the swine feces/urine by the larvae was about 2-3 days.

The number of larvae was decided according to the amount of pig feces in each second Petri dish. Namely, it was estimated how many larvae could feed on the amount of pig feces to estimate the number of larvae to be transferred into each second Petri dish. Generally, the larvae bred in a first Petri dish were placed into a second Petri dish. Each second Petri dish was, but not limited to, a large container having a length of 60-80 cm, a width of 30-50 cm, and a height of 8-14 cm.

Furthermore, since two-stage breeding is used from hatching of the eggs through growing of the larvae, the growing speed of the larvae can be increased. Further, the volume of cultivating material received in each first Petri dish (small container) is less than the pig feces received in each second Petri dish (large container), allowing observation of hatching of the eggs and growth of the larvae while assisting in adjustment and control of the first-stage breeding. The hatching rate and growth of the larvae are increased. The problems of low hatching rate and slow growth or even death of larvae resulting from difficulties in control of using large breeding containers are, thus, avoided. The costs of workers and other expenditures for fixing the problems are cut.

In the method for treating swine feces/urine according to the present invention, suitable breeding conditions are given in the breeding procedures from imagoes to larvae of *Musca Domestica*. Thus, the imagoes and larvae of *Musca Domestica* can grow in suitable environments. Furthermore, the two-stage breeding increases the growing speed of the larvae, shortens the breeding time, increases the yield, and improves the quality of the larvae, assisting in feeding and decomposition of the swine feces/urine by the larvae.

On the other hand, the method according to the present invention rapidly treats swine feces/urine in an environmentally-friendly way by using larvae of *Musca Domestica* such that discharge of the swine feces/urine into water sources, such as rivers, and subsequent pollution are avoided. Furthermore, compared to conventional composting method that requires 4-5 months, the method according to the present invention can decompose the swine feces/urine in 5-7 days by using *Musca Domestica* (from laying eggs through decomposition by the larvae), greatly reducing the time for treating swine feces/urine. Further, the smell of swine feces/urine gradually disappears along with decomposition by the larvae of *Musca Domestica*. There is almost no smell after decomposition of the swine feces/urine, avoiding pollution to the environmental air. Further, since the smell of swine feces/urine gradually disappears and since the second Petri dishes can be placed on a special indoor shelf covered by a housing, attraction of mosquitoes and flies that occur in conventional composting method is avoided. Thus, the environment can be maintained clean, tidy, and sanitary. Further, the tools and equipment used in the method for treating swine feces/urine are simple and inexpensive. Thus, the swine feces/urine can be treated at low costs. Furthermore, the tools and equipment occupy a small area and can be easily operated by the swine cultivators, allowing mass-scale treatment of swine feces/urine.

Although specific embodiments have been illustrated and described, numerous modifications and variations are still possible without departing from the essence of the invention. The scope of the invention is limited by the accompanying claims.

The invention claimed is:

1. A method for treating swine feces/urine comprising:
breeding and growing imagoes of *Musca Domestica* in an environment having a temperature of 18-35° C. and having a humidity of 50-80%, with the imagoes of *Musca Domestica* laying eggs in the environment;
transferring the eggs of *Musca Domestic* into a cultivating material, with the cultivating material including at least one product of soybean or milk, with the eggs of *Musca Domestica* being bred at a temperature of 20-35° C. until hatching into larvae; and
placing the larvae of *Musca Domestica* on swine feces/urine of a thickness of 4-10 cm at a temperature of 20-35° C. for 2-3 days, with the larvae feeding on and decomposing the swine feces/urine.

2. The method as claimed in claim 1, with placing the larvae of *Musca Domestic* on the swine feces/urine including placing the larvae of *Musca Domestica* on the swine feces/urine having a water content of 80-95% by weight.

3. The method as claimed in claim 1, with placing the larvae of *Musca Domestic* on the swine feces/urine including placing the larvae of *Musca Domestica* on the swine feces/urine having a water content of 92% by weight.

4. The method as claimed in claim 1, with breeding and growing the imagoes of *Musca Domestica* including growing the imagoes of *Musca Domestica* in the environment having a temperature of 24-26° C., with the imagoes of *Musca Domestica* laying eggs in the environment.

5. The method as claimed in claim 1, with breeding and growing the imagoes of *Musca Domestica* including growing the imagoes of *Musca Domestica* in the environment having a humidity of 54-56%, with the imagoes of *Musca Domestica* laying eggs in the environment.

6. The method as claimed in claim 1, with the imagoes of *Musca Domestica* laying eggs after the imagoes of *Musca Domestica* has grown 1-3 days.

7. The method as claimed in claim 1, with the eggs of *Musca Domestica* hatching into the larvae in 1-2 days.

8. The method as claimed in claim 1, with transferring the eggs of *Musca Domestica* including transferring 2-4 grams of the eggs of *Musca Domestica* per kilogram of the cultivating material.

9. The method as claimed in claim 1, with transferring the eggs of *Musca Domestica* including transferring the eggs of *Musca Domestica* into the cultivating material in a Petri dish.

10. The method as claimed in claim 1, with transferring the eggs of *Musca Domestica* including transferring the eggs of *Musca Domestica* into the cultivating material having a water content of 80-95% by weight.

11. The method as claimed in claim 1, with transferring the eggs of *Musca Domestica* including transferring the eggs of *Musca Domestica* into the cultivating material having a water content of 92% by weight.

12. The method as claimed in claim 1, with transferring the eggs of *Musca Domestica* including transferring the eggs of *Musca Domestica* into the cultivating material including milk powders.

13. The method as claimed in claim 1, with placing the larvae of *Musca Domestica* on the swine feces/urine including placing the larvae of *Musca Domestica* on the swine feces/urine received in a Petri dish.

* * * * *